United States Patent [19]

Edwards et al.

[11] Patent Number: 5,385,544
[45] Date of Patent: Jan. 31, 1995

[54] BPH ABLATION METHOD AND APPARATUS

[75] Inventors: Stuart D. Edwards, Los Altos; Hugh R. Sharkey, Redwood City; Ingemar H. Lundquist, Pebble Beach; Ronald G. Lax, Grass Valley; Bruno Strul, Palo Alto, all of Calif.

[73] Assignee: Vidamed, Inc., Menlo Park, Calif.

[21] Appl. No.: 61,072

[22] Filed: May 14, 1993

Related U.S. Application Data

[63] Continuation-in-part of Ser. No. 929,638, Aug. 12, 1992, abandoned, and a continuation-in-part of Ser. No. 12,370, Feb. 2, 1993, Pat. No. 5,370,675.

[51] Int. Cl.$^6$ ............................................. A61B 17/20
[52] U.S. Cl. .................................... 604/22; 604/164; 606/47; 607/101; 607/113
[58] Field of Search ............................ 604/19–22, 604/53, 164, 280; 128/24 AA; 606/39, 45, 47; 607/96, 98, 99–102, 113, 115, 116, 138, 156

[56] References Cited

U.S. PATENT DOCUMENTS

Re. 32,066  1/1986  Leveen .
1,879,249   9/1932  Hansaker .

(List continued on next page.)

FOREIGN PATENT DOCUMENTS

| | | |
|---|---|---|
| 10858/92 | 8/1992 | Australia . |
| 2121675 | 5/1990 | Japan . |
| WO911213 | 8/1991 | WIPO . |
| WO92/10142 | 6/1992 | WIPO . |
| 9210142 | 6/1992 | WIPO .................................. 604/22 |
| WO93/25136 | 12/1993 | WIPO . |

OTHER PUBLICATIONS

Blute, Michael L. et al, *Mayo Clinic Proceedings*, 67:417–421 (1992).

Bruskewitz, Reginald, *Mayo Clinic Proceedings*, 67:493–495 (1992).
Chang, Raymond J. et al, *American Heart Journal*, 125: 1276–1283 (May, 1993).
*Standard Urology Product Catalog*, CIRCON ACMI: Stanford (1992).
Cosman, Eric R. et al, *Stereostatic and Functional Neurosurgery*, pp. 2490–2499 (Date Unknown).
Diasonics, Brochure DIA 2000 171 CRF May 1988.
U.I. Dept. of Health and Human Services, *MMWR*, 41:401–404 vol. 41, No. 23, (Jun. 12, 1992).
Perinchery, Narayan, "Neoplasms of the Prostate Gland." pp. 378–409. (Date Unknown).
Scala, Stephen M. et al, *Cowen: Industrial Strategies* (1991).
*Urology*, 5th Ed., Storz, Jan. 1992.

*Primary Examiner*—C. Fred Rosenbaum
*Assistant Examiner*—Chalin Smith
*Attorney, Agent, or Firm*—Oblon, Spivak, McClelland, Maier & Neustadt

[57] ABSTRACT

A method and an apparatus is disclosed for delivering controlled heat to perform ablation to treat the benign prosthetic hypertrophy or hyperplasia (BPH). According to the method and the apparatus, the energy is transferred directly into the tissue mass which is to be treated in such a manner as to provide tissue ablation without damage to surrounding tissues. Automatic shut-off occurs when any one of a number of surrounding areas to include the urethra or surrounding mass or the adjacent organs exceed predetermined safe temperature limits. The constant application of the radio frequency energy over a maintained determined time provides a safe procedure which avoids electrosurgical and other invasive operations while providing fast relief to BPH with a short recovery time. The procedure may be accomplished in a doctor's office without the need for hospitalization or surgery.

6 Claims, 6 Drawing Sheets

U.S. PATENT DOCUMENTS

| | | |
|---|---|---|
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |
| 2,047,535 | 7/1936 | Wappler . |
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. . |
| 3,595,239 | 7/1971 | Petersen . |
| 3,598,108 | 8/1971 | Jamshidi et al. . |
| 3,682,162 | 8/1972 | Colyer et al. . |
| 3,828,780 | 8/1974 | Morrison et al. . |
| 3,835,842 | 9/1974 | Iglesias . |
| 3,840,016 | 10/1974 | Lindemann . |
| 3,850,175 | 11/1974 | Iglesias . |
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,136,566 | 1/1979 | Christensen . |
| 4,137,920 | 2/1979 | Bonnet et al. . |
| 4,154,246 | 5/1979 | Leveen . |
| 4,204,549 | 5/1980 | Paglione et al. . |
| 4,228,809 | 10/1980 | Paglione ............................ 607/156 |
| 4,267,828 | 5/1981 | Matsuo . |
| 4,295,467 | 10/1981 | Mann et al. . |
| 4,307,720 | 12/1981 | Weber . |
| 4,311,145 | 1/1982 | Esty . |
| 4,311,154 | 1/1982 | Sterzer et al. . |
| 4,312,364 | 1/1982 | Convert et al. . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1983 | Cosman . |
| 4,448,198 | 5/1984 | Turner . |
| 4,452,236 | 6/1984 | Utsugi . |
| 4,470,407 | 9/1984 | Hussein . |
| 4,494,539 | 1/1985 | Zenitani et al. . |
| 4,552,554 | 11/1985 | Gould et al. . |
| 4,562,838 | 1/1986 | Walker . |
| 4,565,200 | 1/1986 | Cosman . |
| 4,568,329 | 2/1986 | Mahurkar . |
| 4,580,551 | 4/1986 | Siegmund et al. . |
| 4,594,074 | 6/1986 | Andersen et al. . |
| 4,601,296 | 7/1986 | Yerushalmi . |
| 4,612,940 | 9/1986 | Kasvich et al. . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |

(List continued on next page.)

U.S. PATENT DOCUMENTS

| | | |
|---|---|---|
| 4,805,616 | 2/1989 | Pao . |
| 4,813,429 | 3/1989 | Herzlia et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,047 | 9/1989 | Chou et al. . |
| 4,872,458 | 10/1989 | Kamehira et al. . |
| 4,887,615 | 12/1989 | Taylor . |
| 4,893,623 | 1/1990 | Rosenbluth . |
| 4,896,671 | 1/1990 | Cunningham et al. . |
| 4,905,667 | 3/1990 | Foerster et al. . |
| 4,907,589 | 3/1990 | Cosman . |
| 4,911,148 | 5/1990 | Sosnowski et al. . |
| 4,911,173 | 3/1990 | Terwilliger . |
| 4,919,129 | 4/1990 | Weber et al. . |
| 4,920,978 | 5/1990 | Colvin . |
| 4,932,958 | 6/1990 | Reddy et al. . |
| 4,936,281 | 6/1990 | Stasz . |
| 4,943,290 | 7/1990 | Rexroth . |
| 4,946,449 | 8/1990 | Davis . |
| 4,949,706 | 8/1990 | Thon . |
| 4,950,267 | 8/1990 | Ishihara et al. . |
| 4,955,377 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,998,932 | 3/1991 | Rosen . |
| 4,998,933 | 3/1991 | Eggers et al. . |
| 5,002,558 | 3/1991 | Klein et al. . |
| 5,007,437 | 4/1991 | Sterzer . |
| 5,007,908 | 4/1991 | Rydell . |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber et al. . |
| 5,035,696 | 7/1991 | Rydell . |
| 5,057,105 | 10/1991 | Malone et al. . |
| 5,057,106 | 10/1991 | Kasevich et al. . |
| 5,059,851 | 10/1991 | Corl et al. . |
| 5,071,418 | 12/1991 | Rosenbaum . |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,116,615 | 5/1992 | Gokeen et al. . |
| 5,120,316 | 6/1992 | Morales et al. . |
| 5,122,137 | 6/1992 | Lennox ................... 606/42 |
| 5,135,525 | 8/1992 | Biscoping et al. . |
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,197,963 | 3/1993 | Parins ................... 606/41 |
| 5,201,732 | 4/1993 | Parins et al. . |
| 5,220,927 | 6/1993 | Astrahan et al. . |
| 5,228,441 | 7/1993 | Lundquist . |
| 5,234,004 | 8/1993 | Hascoet et al. ................ 607/102 |
| 5,235,964 | 8/1993 | Abenaim . |
| 5,249,585 | 10/1993 | Turner et al. ................ 607/99 |
| 5,257,451 | 11/1993 | Edwards et al. . |
| 5,281,218 | 1/1994 | Imran . |
| 5,300,069 | 4/1994 | Hunsberger et al. . |
| 5,300,099 | 4/1994 | Rudie . |

BPH ABLATION METHOD AND APPARATUS

RELATIONSHIP TO COPENDING APPLICATION

This application is a continuation-in-part of copending application Ser. No. 07/929,638 filed Aug. 12, 1992 now abandoned and Ser. No. 08/012,370 filed Feb. 2, 1993, now U.S. Pat. No. 5,370,675 the entire contents of which are hereby incorporated by reference.

BACKGROUND OF THE INVENTION

1. Field of the Invention

This invention is directed to a unique method and device for delivering controlled heat to perform ablation to treat benign prosthetic hypertrophy or hyperplasia (BPH). The method and the apparatus deliver this controlled heat into tissue penetrated by devices such as those disclosed in the copending above-referenced applications.

2. Discussion of Background

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 30,000 patients per year undergo surgery for removal of prostatic tissue in the United States. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia associated morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, etc.) which is not without significant consequences. In addition, a significant number of patients with symptoms sufficiently severe to warrant surgical intervention are poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound) and high energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid supply catheter opening at the specific target tissue.

SUMMARY OF THE INVENTION

It is a principal object of the present invention to provide a method and an apparatus which delivers controlled heat to target tissue through intervening tissues without substantially heating or affecting those intervening tissues. The target tissues are selected for medical action such as tissue destruction. The destruction is limited to precise preselected sites to minimize trauma and achieve a greater medical benefit.

One of the other principal objects of the invention is to provide a method and an apparatus for precise tissue destruction of body tissues by delivering therapeutic energy directly into the target tissue while minimizing effects on its surrounding tissue.

Another object of the invention is to provide a method of thermal destruction which is automatically controlled so as to shut off when a surrounding environment exceeds a predetermined temperature.

It is another object of the invention to provide a system for delivering power limited over a particular frequency range and limited over a particular power range for a preselected period of time in order to control temperatures in the adjacent tissues to the target tissue and in order to provide parameters of power delivery so that the applied energy does not affect body organs in the vicinity of the prostate and which do not affect any nervous system elements in the vicinity of said prostate.

It is a further object of the present invention to provide a timed application of RF power at a selected voltage and a selected frequency range to be delivered through a catheter. The type of catheter used includes a probe having a stylet guide housing with at least one stylet port in a side wall and a guide means for directing a flexible stylet outward through a stylet port and through intervening tissues at a preselected angle into target tissue.

It is also an object of the present invention to provide a method and a system which monitors the temperature in the environment of the probe end of the catheter by use of thermal sensors attached proximal to the flexible stylets and proximal to the stylet port wherein each of these sensors provide a feedback indicating the display of the temperature. The invention also provides cut-off of RF power when the temperature of any one of the sensors exceeds a respective predetermined maximum value.

It is also an object of the present invention to provide temperature measurement in adjacent organs of the body of a patient with additional sensors being used to monitor the effect of application of RF power on adjacent portions of the body.

It is a further object of the present invention to provide a voltage delivery system and method which is based upon a calibrated delivery of power which calibration is based upon an impedance typical of a human body.

It is a further object of the present invention to provide for a method of application of a controlled RF power for a predetermined period of time having automatic switch off provisions based upon safety temperature limits within the immediate environment of a catheter delivering the RF voltage and within body organs adjacent to the area of the prostate.

DESCRIPTION OF THE PREFERRED EMBODIMENTS

The method of the present invention provides a precise controlled delivery of RF energy to a tissue targeted for treatment or destruction. The generated power is delivered by means of a catheter providing a stylet which includes a solid or hollow probe adapted to be passed from a catheter port through normal tissue to a target tissue. Typically the stylet is of the type disclosed in copending patent application Ser. Nos. 07/929,638 and 08/012,370. A stylet is shaped in order to facilitate easy passage through the issue and may be composed of a thin wire or rod or can be a thin hollow tube or other shape having a longitudinal lumen for introducing fluids or for removing materials. The stylet is usually and preferably formed with sharpened and reduced resistance when it is pushed through the tissue to the target site. The stylet is designed, according to the present invention, as a radio frequency electrode.

The method of the present invention provides an improved precision and control of medical treatment for destroying cells of medically targeted tissue throughout the body. These cells may be within or external to particular body organs. Most particularly the method and the device for delivering the powers useful for treating benign prostate hyperplasia (BPH) and the device and its use as described in the preferred embodiment are designed specifically with respect to BPH. It will be readily apparent to a person of skill in the art that the device and the method can be used to destroy body tissue and any other body cavity or tissue locations that are accessible by percutaneous or endoscopic catheters and is not limited to the prostate. Applications of the device and the method in all of these organs and tissues are intended to be included within the scope of this invention.

BPH is a condition which arises from the benign replication and growth of cells in the prostate, forming glandular and stromal nodules which expand the prostate and constrict the opening of the prosthetic urethra. Glandular modules are primarily concentration within the transition zone, and stromal nodules within the peri-urethral region. Traditional treatments of this condition have included surgical removal of the entire prostate gland, digital removal of the adenoma, as well as transurethral resection of the urethral canal and prostate to remove tissue and widen the passage way. One significant serious complication associated with the latter method is iatrogenic sterility. More recently, laser treatments have been applied to remove tissue, limiting bleeding and loss of body fluids. Balloons have also been expanded within the urethra to enlarge its diameter, with and without heat, but have been found to have significant limitations.

Microwave therapy has been provided with some success by positioning a microwave antenna within the prosthetic urethra and generating heat in the tissues surrounding the urethra with a microwave field. Coolants are sometimes applied within the catheter shaft to reduce the temperature of the urethral wall. This necessitates complicated mechanisms to provide cooling of the immediately adjacent tissues while at the same time generating heat in the more distant prosthetic tissue. This technique is similar to microwave hyperthermia. Similarly, radio frequency tissue destruction with electrodes positioned within the urethra has a limited applicability since it necessarily exposes the urethral wall to destructive temperatures. To avoid this, low temperature setting is required to protect the urethra and must be so low that the treatment time required to produce any useful effect is unduly extended, e.g., up to three hours of energy application.

In a preferred embodiment of the present invention, the urethra is used to access the prostate and position RF stylets directly into the tissues or nodules to be destroyed. The portion of the stylet conductor extending from the urethra to the target tissue is enclosed within a longitudinally adjustable sleeve which prevents exposure of the tissue adjacent to the sleeve to the RF current. Therefore, the ablative destruction is confined to the tissue targeted for destruction, namely those causing constriction. More particularly, according to the present invention the method of delivering power to the electrode stylets is controlled within a power range and frequency range and is limited by a series of temperature sensors positions proximal to the stylets in order to ensure complete protection of surrounding tissues. This is made possible by an automatic cutoff of RF energy to the system upon the sensing of any one of the sensors exceeding a predetermined safe temperature for the region being treated. The method also features automatic power cut-off using additional sensors placed proximal to body organs adjacent to the tissue being treated in order to avoid damage to those adjacent body organs due to increased organ temperature.

Figure 1:
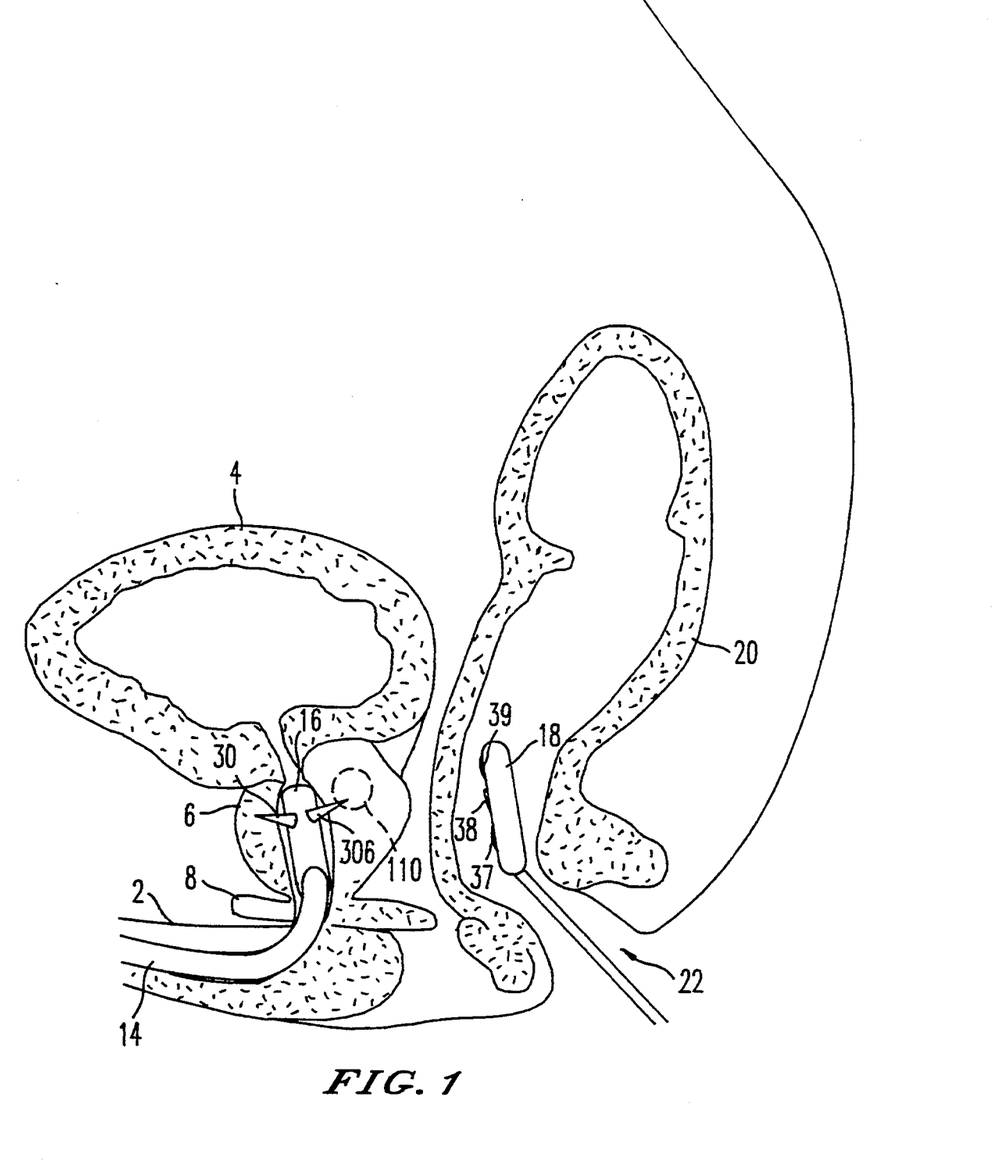
FIG. 1 is a cross-sectional drawing of the lower male anatomy showing the placement of a catheter and a prostate probe with the catheter delivering power according to the preferred embodiment of the method of the present invention.

FIG. 1 is the schematic cross-sectional drawing of the lower male anatomy during the use of a typical device for applying the controlled energy to the treated tissue generated and delivered according to the method and apparatus of the present invention. The urethra 2 extends from the urinary bladder 4 through the prostate 6 and a urogenital diaphragm 8. BPH is a condition characterized by constriction of the portion of the prosthetic urethra caused primarily by proliferation of benign glandular and stroma cells in the prostate. These nodules press the wall of the urethra inwardly restricting the urethral diameter, and may at times press normal tissue outwardly possibly enlarging the prostate. Traditional treatment, short of removal of the prostate, have included either removal of tissue from the urethra to enlarge its lumen by resection or laser tissue destruction, or by expansion and heating of the tissues surrounding the urethra and to a temperature which causes cell damage. The latter method is intended to reduce the swelling or enlargement of the prostate, and restore the urinary passage to at least a portion of its former diameter.

A catheter 14 with a stylet guide 16 is passed downwardly through the urethra into the prostate. The position of the guide 16 is precisely controlled, using an ultrasound image, for example, obtained from signals received from the conventional ultrasonic transducer 18 inserted into the rectum 20 adjacent to the prostate through the anal opening 22. The guide facilitates easy positioning of the stylet 17 into a precise location under ultrasonic imaging. The guide 18 may also contain sensors 37, 38 and 39 for sensing, within the bowel region, any effects from heating tissue as will be described later. Optionally, the sensors 37, 38 and 39 can be a part of a separate instrument placed into the rectal area after removal of an ultrasonic probe and after the catheter 14 and stylet guide 16 have been positioned. The FIG. 1 illustrates two stylets 306 and 308 with the stylet 306 having its end penetrated into the tissue area 170 which represents tissue to be ablated.

Figure 2:
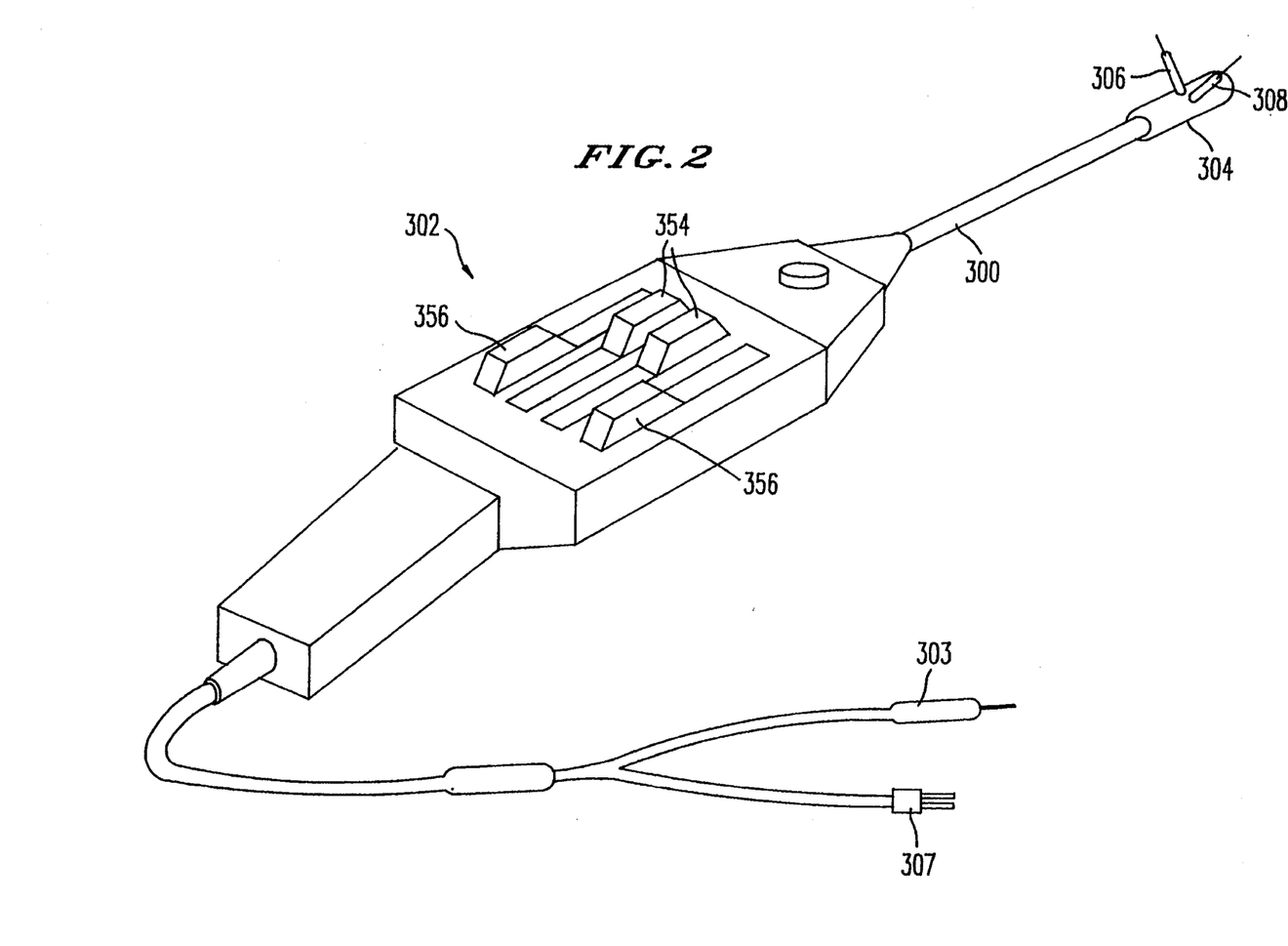
FIG. 2 is a top view of a two stylet embodiment of an RF ablation catheter utilizing the power application of the present invention.

FIG. 2 is a top view of a two stylet embodiment of an ablation catheter of FIG. 1 used to deliver power from the preferred method and apparatus of the present invention. The flexible catheter 300, attached to handle 302, has a terminal stylet guide 304 with two stylets 306 and 308. The handle has stylet sleeve cap 356 and electrode cap 354. The handle is also connected to a RF power connector 303 to be discussed in detail hereinafter. Also shown is a connection for a thermoconnector 307. The portions of the catheter 300 leading from the handle 302 to the stylet guide 304 can optionally have a graduated stiffness. For example, the catheter can be designed to be more stiff near the handle and more flexible near the tip or any other stiffness profile desired. The catheter can be constructed of an inner slotted stainless steel tube with an outer flexible sleeve such as is described in copending application Ser. No. 790,648 filed Aug. 11, 1991, the entire contents of which are incorporated herein by reference. It can also be made of a coiled or braided wire to which an outer sleeve is bonded. The stylet of FIG. 2 is described in the copending application Ser. No. 08/012,370 filed Feb. 2, 1993.

Figure 3A:
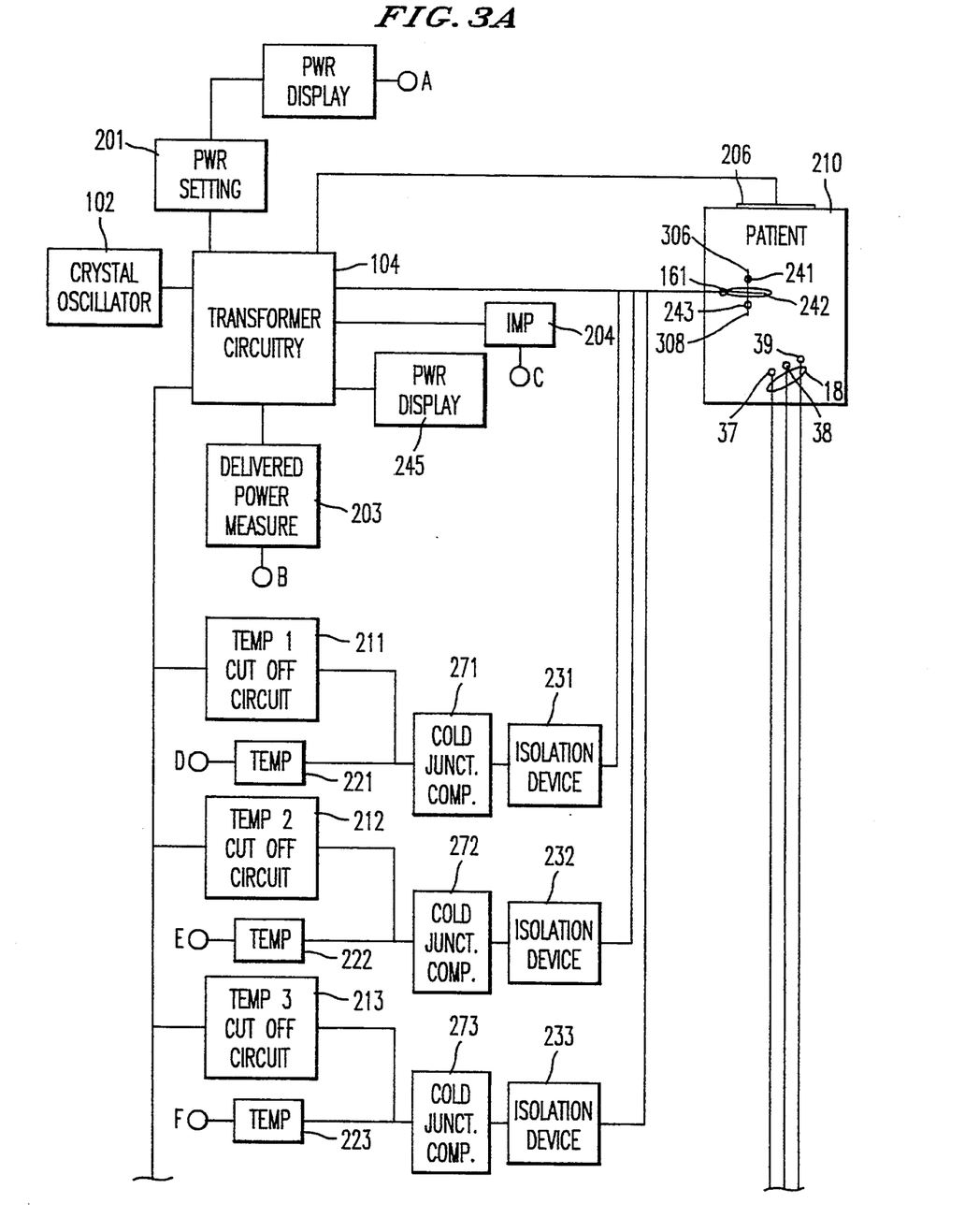
FIG. 3 is a schematic of the power supply for the delivery system of the method of the present invention.
Figure 3B:
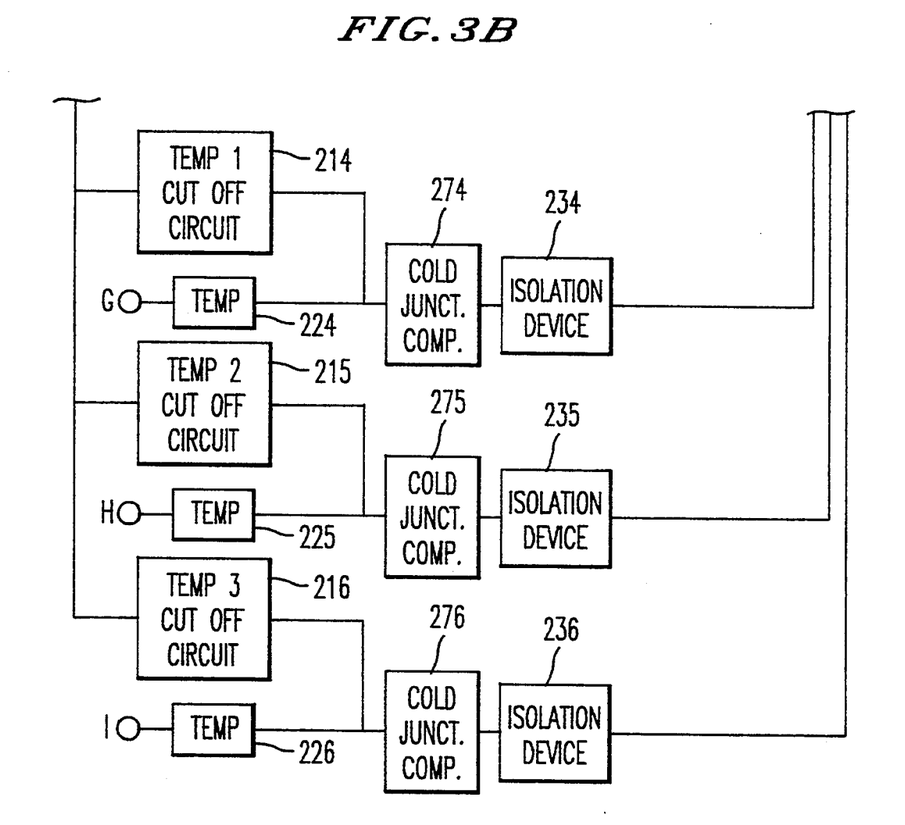

The power delivery method of the present invention is enabled by the power supply delivery system shown in the schematic of FIG. 3.

Figure 2A:
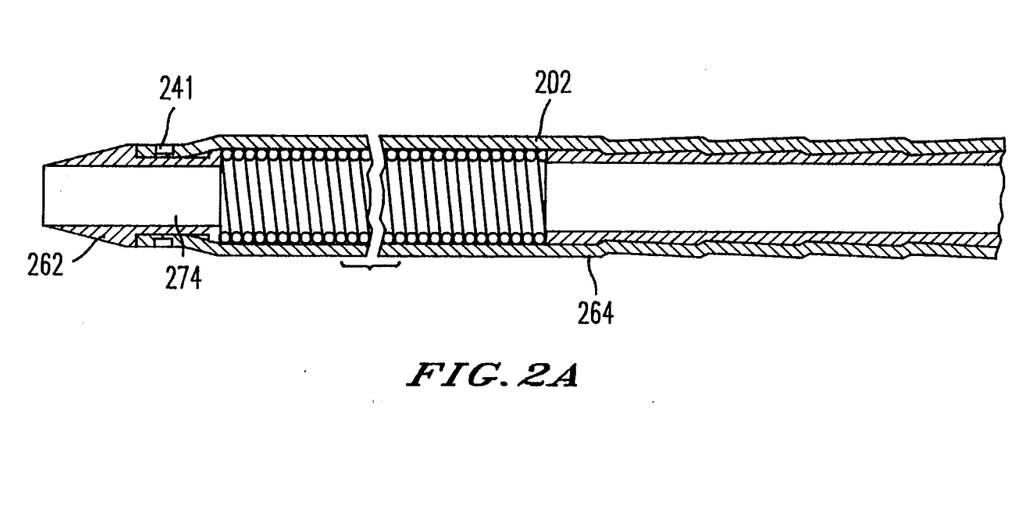
FIG. 2A is a side-view of a non-conductive sleeve covering each stylet of FIG. 2.

The block labelled 210 illustrates connections to the patient with the inserted stylet guide 16 and the transducer probe 18 having the sensors 37, 38 and 39 in a manner similar to the FIG. 1. The stylet guide 16 has two stylets with the illustrated sensors 241 and 243 being respectively attached in the vicinity of the stylet. More particularly, in a preferred embodiment, the stylets 306, 308 of FIG. 2 each include a non-conductive sleeve as illustrated in FIG. 2A. This non-conductive sleeve is discussed in detailed in copending application Ser. No. 08/012,370. For purposes of the present application, the non-conductive sleeve has a tapered leading tip 262 and a rigid proximal portion 264. The center portion or the inner lumen 274 of the non-conductive sleeve 202 receives the stylet 306, 308. A temperature sensor 241 is mounted on the tip. The mounting 243 shown schematically in FIG. 3 corresponds to the other of the stylets and would be identical to the placement of the sensor 241. The third illustrated sensor in the stylet guide is labelled 242 and corresponds to a placement inside the guide near the surface. The stylet guide is illustrated with the three sensors 241-243 which send temperature signals through the isolation device 231-233, respectively, in order to provide a temperature measurement at 221, 222, and 223, respectively.

The heating of the stylets 306 and 308 is accomplished through the generation of RF power by means of the crystal oscillator 102 and the transformer circuitry 104 schematically shown in FIG. 3. The crystal oscillator in a preferred embodiment delivers effectively a 482 KHz rf power to the stylet guide and more particularly to the stylets 306 and 308, respectively. The transformer circuitry is calibrated for an impedance of 100 ohms. The impedance is based upon a median impedance expected in human patient measurements typical with placements of stylets in the urethra. In the actual operation of the circuitry of FIG. 3, the impedance varies from the calibrated impedance and this is measured by circuit 204. Because the delivery of the rf energy is monopolar, each patient must have an indifferent electrode 206 to complete the circuit. Typically, these electrodes are large patches which are placed on patient's back and are held by adhesive.

In a preferred arrangement, the transformer circuitry is capable of 16 watts although the normal range of application for purposes of the isolated tissue ablation encountered in BPH is between 5 and 7 watts which is typically applied for three minutes.

The limits on the operation of the circuitry, aside from operator settings and frequency and power maximums, are determined by sensors 241, 242 and 243 associated with the stylet guide 16 and sensors 37, 38 and 39 associated with the rectal probe 16. The processing of the outputs from the sensors 241, 242, 243 and 37, 38 and 39 are identical as shown by the isolation devices 231 to 236 and the temperature measurements 221-226, respectively. The isolation device 231-236 involves a 1500 voltage isolation circuit which in a preferred embodiment is a Burr-Brown isolation device ISO 122JP. The output from this isolation device 231-236 is fed through cold junction compensators 271-276 to the temperature measurement 221-226 circuits and to temperature cutoff circuits 211-216. Each of the isolation devices 231-236 are identical as are the temperature measurement devices 221-226. Each cold junction compensation structure 271-276 provides absolute temperature measurement readings in degree Celsius. Although the circuitry is the same for each of the temperature cutoff circuits 211-216, each of these cut-off circuits have a different temperature limit or may have a different limit. Based upon physiological evaluation to insure against excess overheating in the environment of the tissue being destroyed and in adjacent organs, the following limits have been set to provide protection to the patient. The sensor cutoff for circuits 211 and 212 correspond to the sensors 241 and 243 and have a setting of 90° C. as a cutoff. To illustrate, a temperature of 60° C. is sufficient to provide for tissue protein dephasing which provides for the destruction of the tissue. The temperature in the guide 16, as detected by sensor 242 is set by the cutoff circuit 213 and a temperature of 45° C. This insures that no damage occurs to the urethra in which the guide is placed. In other words, the material inside the urethra will not be destroyed if the temperature is maintained at 45° or less. It must be noted that if any one of the cutoff circuits operate, then the entire system is automatically shut-off regardless of any operator decisions. Thus, if either the sensors 241 or 243 reach 90° C. or if sensor 242 reaches 45° the device will shut off.

The purpose, as discussed previously, of the sensors 37, 38 and 39, which are typically located in a rectal probe 16, is to prevent adjacent organ damage and particularly to protect against overheating of the bowel. This temperature setting in a preferred embodiment is set at 40° C. for each of the sensors 37, 38 and 39. Forty degrees C is a temperature which is only slightly above normal body temperature (37.5° C.). Thus, once again if, any of the sensors 37, 38 and 39 exceed their predetermined cut-off limit, the entire operation of delivery of the power to the stylets 306, 308 is shut down.

Also shown at FIG. 3 is a repetition rate adjuster 245 which can be used to provide a pulsed output delivery of energy to allow for variation in time of delivery of energy based upon physiologic considerations. The pulse output delivery of energy allows for electronic pulsing to provide the ability to adjust intervals between applications of energy in order to provide bursts of energy which, when applied for a short time, does not cause any of the temperature sensors to exceed their predetermined value but which delivers sufficient energy to kill cells in the in the tissue volume selected for a lesion in the vicinity of the stylet. After the application of such a spike of energy, an interval before the next spike allows a total energy application to be of such a value as to not affect adjacent tissue areas or adjacent organs. In other words, the application of electronic pulsing provides an opportunity for applying an energy spike to have a localized destructive effect in a short period of time while at the same time restricting an overall total energy during a predetermined period so as to not significantly affect tissue masses beyond the desired lesion volume and other body organs. The spike will be applied for a controlled short period of time and have a controlled maximum level so that in an overall cycle of, for example three minutes, the total energy would either be the same as or less than the energy applied during a continuous application which energy is calculated not to trigger any of the temperature sensor cutoff switches.

The electronic pulsing provides an opportunity, when necessary and when desired, to more efficiently destroy cells in a very localized targeted area and still maintain the safety of the method and the apparatus. The temperature limits of the sensor are not exceeded because, as indicated above, the total energy applied is not greater than that which would be applied in a continuous operation.

The monitoring of the application of the electronic pulsing can be accomplished manually based on observed temperatures on the monitor. That is, an operator could observe the approach of a temperature to the cutoff limit and stop the application of energy until a cooling off occurs and then reapply the pulsing energy. Alternatively, such monitoring could be performed electronically based on preset parameters controlled by the necessary spiking of energy required to destroy a certain cell area and the subsequent electronic monitoring of temperature increase and temperature decrease rates. None of these electronic pulsing steps either accomplished manually or electronically based upon physiological considerations would affect the safety of the patient because each of the temperature cutoff switches would still function to automatically shut down the entire power supply if any one of those temperature sensors either in adjacent mass tissue of the stylets or the sensor in the catheter guide in the urethra or any adjacent body organ would exceed its preset safety temperature. Electronic pulsing either accomplished manually or through an electronic physiological scheme provides an opportunity through the pulse repetition rate adjustor 245 to maximize the efficiency of the destruction of the target mass tissue without adversely affecting the surrounding tissue or adjacent body organs.

Figure 4:
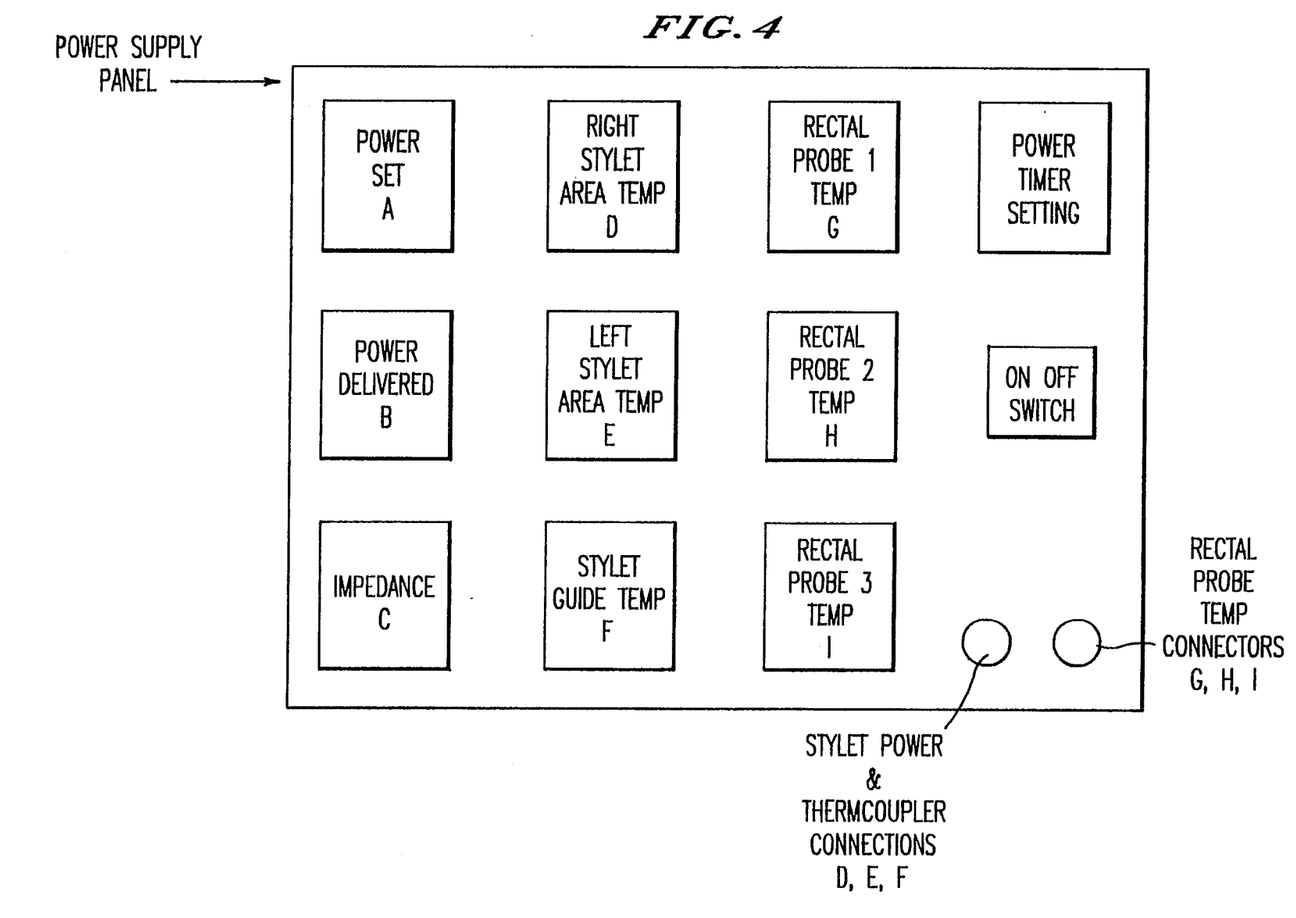
FIG. 4 is a view of the front panel of the power delivery system in accordance with the present invention.

The operation of the power delivery system in accordance with the method of the present invention will now be discussed in conjunction with FIGS. 3 and 4 with FIG. 4 representing the front panel of a preferred embodiment of the operating system. The relationship between FIGS. 3 and 4 is such that the outputs from the various measurements in FIG. 3 labeled A–I refer to the displays A–I in the front panel of the power supply of FIG. 4. Display A shows the power which is set by an operator to be delivered by the supply and the transformer circuitry 104 in particular. There is another power display B which is a display of the actual delivered power. As discussed previously, the power supply was calibrated for an impedance load of 100 ohms. Any variance between the impedance of 100 ohms and a particular patient will bring about slight variations between the power which is set in the display A and that which actually delivered and measured by circuitry 203 and displayed at B. In order to detect circuit completion, impedance measure 204 applies a display of the impedance to the display panel C on the front of the device. The remaining displays D–I associated with the temperature measuring devices 221–226 provide a display on the front panel of the temperature of each of the sensors 241–243 from the stylet guide 16 and the sensors 37–39 from the probe 18. Appropriate labeling on the front panel of FIG. 4 readily identifies which of the sensors is being monitored. It must be emphasized that the monitoring by the operator of the temperature is completely independent of the operation of the cutoff circuitry 211–216 which, as has been previously indicated, operates to automatically shut off the system regardless of any action taken by the operator. No further operation or restarting will occur until the temperatures of sensors decrease below their cutoff limit values.

In a preferred embodiment, connectors 47 and 48 provide for attachment to the various probes with one of the connections 47 providing an output to deliver power to the stylet as well as provide a sensor connection to receive temperature signals from the three sensors 241, 242 and 243. Separate connector 48 receives the temperature delivered from sensors 37, 38 and 39.

Although there have been illustrated three sensors associated with the stylet guide and three sensors associated with the rectal probe 18, it can be readily seen that additional sensors or differently placed sensors may be used with temperature cutoff limits being set in recognition of the physiological implications resulting from temperatures at other parts of the body.

Also in accordance with a preferred embodiment, the sensors 37–39 and 241–243 are thermocouples although other forms of temperature sensors may be contemplated.

The RF energy frequency delivered by the preferred embodiment of the FIGS. 3 and 4 has, as mentioned previously, a frequency of 482 KHz. Other frequencies are available with the range being determined by frequencies which do not substantially effect any physiological change within the body particularly as regard to the nervous system or any sensitive organs in the current path. Using those considerations, the frequency range extends from above approximately 250 KHz in order to avoid damage based solely on the frequency of the signal. Other damage to be avoided of course results from the application of high voltages and large power. Particularly, what must be avoided are large power surges which can cause severe damage. Such large power surges can readily occur in electrosurgery when a particular impedance is being significantly altered as a result of tissue destruction. Such rapid changes in impedance cause extremely high voltages to occur which can severely damage adjacent nervous system elements and neighboring organ functionings resulting in unacceptable rates of impotency.

The present method of power delivery avoids this drastic change in impedance levels and particularly avoids surges of electricity based upon the continuous delivery of constant energy with no significant variation in the impedance of the circuitry.

In the alternate embodiment provided by the operation of the previously discussed pulsing by repetition adjustment, the total energy over any significant period of time remains substantially constant and the impedance level remains constant in sharp contrast to electrosurgery which has tremendously high energy peaks caused by breakdown in impedance which often occurs during the electrosurgery operation without any reliable feedback control.

Tissue ablation in the desired area of treatment, in accordance with the embodiments of the present invention, results from the precise application by way of the stylets of low power substantially constant energy delivery resulting in minimal effect on the adjoining healthy tissue and on neighboring nervous system elements and body organs.

For purposes of treating BPH the method of treatment using the power delivery system of the FIGS. 3 and 4 involves the operator applying an energy level of between 5 and 7 watts for 3 minutes, followed by repositioning of the stylet or stylets to other areas of treatment and the subsequent reapplication for an additional 3 minutes of the same range of energy. The number of applications is determined by the extent and the location of the tissue to be ablated. During each operation, temperature cutoff limitation circuitry affords the necessary protection due to any unexpected rise in temperature and the temperature limitations assure control of the environment immediately adjacent the tissues being treated as well as the urethra and any adjacent organs. The protection of the adjacent organs with respect to temperature rise is provided by the temperature cutoff limits associated with sensors 37, 38 and 39.

Obviously, numerous additional variations and modifications of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A medical probe device for medical treatment of the prostate, comprising:
 a catheter having a stylet guide housing at one end;
 a stylet having a flexible radio-frequency electrode with a sharpened tip and an insulating sleeve that retains the electrode and is movable relative to the electrode;

stylet guide means disposed in the stylet guide housing for retaining and directing the stylet outward through a stylet port in a side of the stylet guide housing;

means for introducing the catheter through the urethra to a zone adjacent to the prostate;

means for advancing the electrode from the catheter through the wall of the urethra into the prostate tissue to be treated such that the sharpened tip of the electrode punctures and penetrates the urethra wall with the sleeve extending through the urethra wall;

means for retracting the insulating sleeve within the prostate tissue to expose a predetermined length of electrode in the prostate tissue;

power supply means connected to the electrode for passing electric current through the electrode until the temperature of the prostate tissue adjacent the predetermined length of electrode is raised to a temperature causing destruction of cells of the prostate tissue; and first temperature monitoring means connected to the power supply means for measuring the temperature of tissue proximal to the prostate and providing a cutoff of the electric current when the monitored temperature exceeds a predetermined value.

2. The medical probe device as set forth in claim 1, wherein the stylet guide housing includes at least two stylet ports and stylets therein.

3. The medical probe device as set forth in claim 1, wherein the power supply is calibrated using an impedance level normally associated with a human male.

4. The medical probe device as set forth in claim 1, and further including second temperature monitoring means connected to the power supply means for measuring the temperature of a body organ in the vicinity of the prostate and providing a cutoff of the electric current when the monitored temperature exceeds a predetermined value.

5. The medical probe device as set forth in claim 4, wherein the first and second temperature monitoring means each includes an isolation device and a cold junction compensator.

6. The medical probe device as set forth in claim 1, wherein the power supply means provides a pulsed electric current and the power supply means includes repetition rate adjustment means for varying the repetition rate of the pulsed electric current.

* * * * *